United States Patent [19]

Rowland et al.

[11] Patent Number: 5,041,100
[45] Date of Patent: Aug. 20, 1991

[54] CATHETER AND HYDROPHILIC, FRICTION-REDUCING COATING THEREON

[75] Inventors: Stephen M. Rowland, Miami; Roger B. Wright, Miramar, both of Fla.

[73] Assignee: Cordis Corporation, Miami Lakes, Fla.

[21] Appl. No.: 345,102

[22] Filed: Apr. 28, 1989

[51] Int. Cl.$^5$ .............................................. A61M 25/00
[52] U.S. Cl. .................................... 604/265; 604/264
[58] Field of Search ................. 604/93, 264, 265, 172; 623/12

[56] References Cited

U.S. PATENT DOCUMENTS

| | | | |
|---|---|---|---|
| 4,042,978 | 8/1977 | Jones et al. | 623/12 X |
| 4,100,309 | 7/1978 | Micklus et al. | |
| 4,119,094 | 10/1978 | Micklus et al. | |
| 4,487,865 | 12/1984 | Balazs et al. | |
| 4,500,676 | 2/1985 | Balazs et al. | |
| 4,557,724 | 12/1985 | Gregonis et al. | 604/265 X |
| 4,642,267 | 2/1987 | Creasy et al. | |
| 4,720,512 | 1/1988 | Hu et al. | 523/112 |
| 4,769,013 | 9/1988 | Lorenz et al. | |
| 4,781,703 | 11/1988 | Walker et al. | 604/264 |
| 4,912,142 | 3/1990 | Vermeulen et al. | 521/105 |
| 4,950,257 | 8/1990 | Hibbs et al. | 604/265 |
| 4,976,703 | 12/1990 | Franetzki et al. | 604/247 |
| 4,977,904 | 12/1990 | Kaufman | 128/856 |

OTHER PUBLICATIONS

Mori et al. entitled, A New Antithrombogenic Material with Long Polyethyleneoxide Chains, vol. XXVIII, Trans. Am. Soc., Artif. Inter. Organs (1982) pp. 459 through 463.

Merrill et al. entitled, Polyethylene Oxide as a Biomaterial, ASAIO Journal, Apr./Jun. 1983, vol. 6, pp. 60 through 64.

Gregonis et al. entitled, Poly(ethylene Glycol) Surfaces to Minimize Protein Adsorption—Journal of the 10th Annual Meeting of the Society for Biomaterials, Washington, D.C., Apr. 27-May 1, 1984, p. 266.

*Primary Examiner*—John D. Yasko
*Assistant Examiner*—Adam J. Cermak
*Attorney, Agent, or Firm*—Gerstman & Ellis, Ltd.

[57] ABSTRACT

A friction-reducing coating may be applied to a base material, for example the outer surface of a catheter, to provide a significant reduction in catheter friction, particularly when the friction-reducing coating is hydrated. The coating comprises an intimate mixture of a structural plastic material, for example polyurethane, and high molecular weight poly(ethylene oxide).

18 Claims, 1 Drawing Sheet

CATHETER AND HYDROPHILIC, FRICTION-REDUCING COATING THEREON

BACKGROUND OF THE INVENTION

For many devices, particularly catheters, it is desirable to reduce friction as the catheter for example is inserted into the body of a patient. In virtually all medical uses of that type, the catheter surface is exposed to moisture from the patient's own body fluids. Thus, injury to tissues of the patient is reduced if the catheter, with a moistened surface, can be advanced with reduced friction into its desired position within the patient. A reduction of friction results in a reduction of the necessary insertion force within the patient, plus a reduced insertion force to install the catheter within a catheter sheath introducer or the like. At the same time, it is important for the catheter to exhibit good antithrombogenic characteristics if it is to be installed in the arteriovenous system of the patient.

To accomplish this, various friction lowering coatings have been applied to catheters and other devices. See for example Micklus et al. U.S. Pat. Nos. 4,119,094; and 4,100,309. See also Balazs et al. U.S. Pat. Nos. 4,500,676; and 4,487,865; Creasy et al. U.S. Pat. No. 4,642,267; and Lorenz et al. U.S. Pat. No. 4,769,013..

In accordance with this invention, an improved hydratable, friction-reducing coating for catheters, or any other desired article, is provided, in which the friction-reducing coating is extremely effective, particularly in the presence of substantial moisture, and also very easy to apply as a coating to a base material without the need of inflammable, toxic, organic solvents to serve as a carrier as the coating is applied to a base material. Instead, a simple, primarily aqueous dispersion of the coating ingredient can be used to apply the coating in safe and simple manner, without the need for any curing step to effect cross-linking. Also, water-dispersable therapeutic agents or the like may be added to the aqueous dispersion as coating ingredients.

Additionally, the components of the friction-reducing coating of this invention may be very nontoxic, and unlikely to set off allergic or other sensitizing reactions in the patient or other user. Likewise, the coating in accordance with this invention can have very low thrombogenicity, making it an excellent candidate for use with an arteriovenous catheter.

Furthermore, the friction-reducing coating of this invention can bond well to selected base materials, depending upon the specific nature of the coating, so that catheters or other articles may exhibit greatly reduced friction under hydrated conditions without loss of the coating through wear, coupled with good acceptability from a toxicological standpoint.

DESCRIPTION OF THE INVENTION

The invention of this application pertains to a friction-reducing coating carried on a base material, for example the outer surface of a plastic catheter, but also on steel items or any other desired instrument or device. In accordance with this invention, the coating comprises an intimate physical mixture of 50 to 98 weight percent of a structural plastic material having hydrophobic characteristics, and 2 to 50 weight percent of poly(ethylene oxide) having a molecular weight of at least 10,000.

A "structural plastic" is defined in this application as a plastic capable of forming a solid structure, such as a coating film, when mixed with the poly(ethylene oxide).

The structural plastic material is preferably an aliphatic polyurethane to avoid any possibility of the generation of aromatic amines within or adjacent a patient. However, other inert, strong hydrophobic plastic materials besides polyurethanes may be used: vinyl resins, polyolefins such as polyethylene or polypropylene and copolymers thereof, elastomers such as latex or KRATON (a product of Shell Chemical Co.), polystyrene, polyesters, polyacrylates, polymethacrylates, phenolic, alkyd, or silicone resins, polyamides, and the like, as well as copolymers thereof.

The poly(ethylene oxide) is admixed without crosslinking in intimately dispersed relation with the structural plastic material to provide a hydrophilic component to the system, which may leach to the surface, or which may be entrapped adjacent the surface to provide a hydrophilic character thereto and reduced friction, particularly when hydrated. Preferably, the molecular weight of the poly(ethylene oxide) is ultra high, being generally at least 100,000 and preferably at least one million or higher, being typically limited to an upper molecular weight limit of about ten million, although there appears to be no absolute upper limit to the molecular weight of poly(ethylene oxide) that may be used. The higher molecular weight materials tend to be more firmly entrapped within the matrix of the structural plastic, possibly with long chain portions extending out of the surface of the structural plastic to provide a permanent, hydrophilic lubricity thereto which does not readily leach or wash away. The coating of this invention has longer life and durability than surfaces merely carrying adsorbed poly(ethylene oxide).

Preferably, about 5 to 20 parts by weight of the structural plastic material, preferably polyurethane, are present in the friction-reducing coating per one part by weight of poly(ethylene oxide).

Polyurethane based materials in accordance with this invention have been found to exhibit excellent adhesion to a base material of polyurethane or steel, particularly stainless steel, for a strong, permanent coating of catheters and medical instruments where desired.

Additionally, the friction reducing coating of this invention may also contain an effective amount of a therapeutic agent, so that, typically, with the coating in contact with the patient, the therapeutic agent can diffuse out of the coating in a continuous, controlled dosage over a substantial period of time, in a manner similar to that described in the commonly owned Rowe U.S. patent application Ser. No. 322,929, filed Mar. 14, 1989.

Specific examples of such therapeutic agents include anti-thrombogenic agents or other agents for suppressing acute thrombosis, stenosis or late restenosis in arteries such as heparin, streptokinase, urokinase, tissue plasminogen activator, anti-thromboxane $B_2$ agents, anti-B-thromboglobulin, prostaglandin E, aspirin, dipyridimol, anti-thromboxane $A_2$ agents, murine monoclonal antibody 7E3, triazolopyrimidine, ciprostene, hirudin, ticlopidine, nicorandil, and the like. Antiplatelet derived growth factor may be used as a therapeutic agent to suppress subintimal fibromuscular hyperplasia at an arterial stenosis site, or any other inhibitor of cell growth at the stenosis site may be used.

The therapeutic agent also may comprise a vasodilator to counteract vasospasm, for example an antispasmodic agent such as papaverine. The therapeutic agent may be vasoactive agents generally such as calcium antagonists, or alpha and beta adrenergic agonists or antagonists. Additionally, the therapeutic agent may include a biological adhesive such as medical grade cyanoacrylate adhesive or fibrin glue, the latter being for example to adhere an occluding flap of tissue in a coronary artery to the wall, or for a similar purpose.

The therapeutic agent in accordance with this invention may be an anti-neoplastic agent such as 5-fluorouracil or any known anti-neoplastic agent, optionally mixed with a controlled release carrier for the agent, for the application of a persistent, controlled release anti-neoplastic agent to a tumor site.

The therapeutic agent may be an antibiotic which may be applied by this invention, optionally in conjunction with a controlled release carrier for persistence, to an infected stent or any other source of localized infection within the body. Similarly, the therapeutic agent may comprise steroids for the purpose of suppressing inflammation or for other reasons in a localized tissue site.

Also, anti-infective agents such as chlorhexidine may be added for improved biocompatibility of articles carrying the coating of this invention.

The coating may contain binders such as quaternary ammonium compounds and/or amino-functional poly(ethylene oxide), to modify the release kinetics of therapeutic agents carried in the friction-reducing coating of this invention.

Poly(ethylene oxide) has the desired, known characteristic of "passivating" a surface toward platelets, and is quite non-thrombogenic. See the article by Mori et al. entitled "A New Antithrombogenic Material with Long Poly(ethylene oxide) Chains," Volume 28 *Trans. Am. Soc. Artif. Intern. Organs* (1982) pages 459 to 463. See also the article by Merril et al. entitled "Poly(ethylene oxide) as a Biomaterial" *ASAIO Journal* April/June 1983 Volume 6, pages 60 to 64. Additionally, see the article by Merrill et al. Volume 28 *Trans. Am. Soc. Artif. Intern. Organs* (1982) pages 482–487.

Thus, the friction-reducing coating of this invention has as an added advantage the capability of greater blood comparability, with reduction of clotting. Also, the coating of this invention provides a reduction in contact damage to body cells, when compared with hydrophobic coatings such as polyurethane.

The therapeutic agent, when used, may constitute any desired mixture of individual pharmaceuticals or the like, for the application of combinations of active agents.

As stated above, the friction-reducing coating of this invention may be applied in any desired manner to a base material such as the outer surface of a catheter. For example, it may be applied by means of a substantially aqueous dispersion followed by drying, preferably with the structural plastic material being present preferably in emulsion form in a concentration of about 2 to 40 percent (weight/volume) and the poly(ethylene oxide) being present in a proportionate concentration depending on its desired concentration in the resulting dried, friction-reducing coating, typically 2 to 100 weight percent, based on the structural plastic material present. If desired, a minor portion of cosolvent or other additives may be provided to the aqueous dispersion, for example an emulsion stabilizer such as triethylamine or another known material in an effective concentration to provide such emulsion stabilization.

Typically, the resulting friction-reducing coating has a thickness of about 0.0001 to 0.05 inch, or thicker if desired.

DESCRIPTION OF DRAWING

In the drawing, an enlarged, fragmentary, perspective view of a catheter is shown, with a portion shown in cross section, said catheter carrying the friction-reducing coating of this invention.

DESCRIPTION OF SPECIFIC EMBODIMENT

Figure 1:
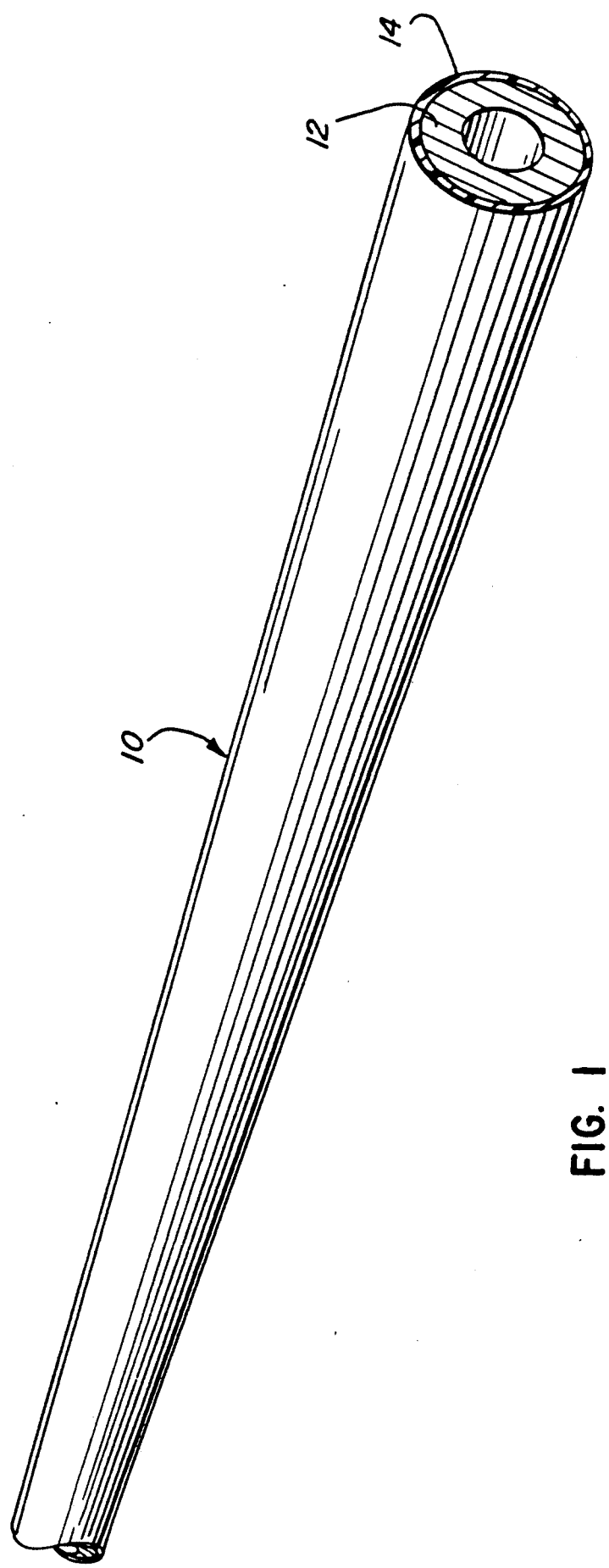

Referring to the drawing, catheter 10 is shown in fragmentary manner, being part of a diagnostic cardiovascular catheter of generally conventional design except as otherwise described herein. Catheter body 12 is made of a polyurethane material, such polyurethane cardiovascular diagnostic catheters being sold by the Cordis Corporation of Miami, Fla.

In accordance with this invention, catheter 10 carries, on the outer surface of body 12, a friction-reducing coating 14 which may typically be of a thickness of 0.0002 to 0.001 inch. Coating 14 may be applied to the catheter by spraying or dipping to apply an aqueous dispersion of the coating ingredients, followed by drying the catheter by incubation, for example at 60 degrees C. for 30 minutes. Coating 14 has been found to spontaneously form a strong bond upon drying with the polyurethane catheter body 12 when an aqueous coating dispersion applied to such a catheter 10 is of the formulation as disclosed in Example 1 below:

EXAMPLE 1

An aqueous dispersion of the following formula was prepared by mixing:

25 ml. of an aqueous emulsion of aliphatic poly(urethane) polymer structural plastic solids in 40 weight percent concentration, said emulsion containing 1 weight percent triethylamine (Neo Rez R967-ICI Resins).

75 ml. of water 100 ml. of a dispersion of poly(ethylene oxide) in one percent concentration in water, having a molecular weight of about 5 million (Polyox WSR Coagulant, N.F. grade-Union Carbide).

The above coating solution thus contains 5 percent by weight of the aliphatic polyurethane, 0.5 percent by weight of the poly(ethylene oxide), and 0.125 percent by weight of triethylamine.

The resulting coating solution may be applied to a commercially available polyurethane cardiovascular diagnostic catheter by spraying or dipping the surface of the catheter with or into the above described coating solution, followed by drying of the coated catheter at 60 degrees C., to obtain a friction-reducing coating on the catheter exterior containing about 91 weight percent of structural polyurethane plastic material, and about 9 weight percent of the poly(ethylene oxide), assuming the triethylamine evaporates, the coating having a thickness of about 0.0002 to 0.0004 inch in thickness.

Such a coating 14 on a polyurethane catheter adheres to the catheter with good strength, and provides very significant reduction in the coefficient of friction of the catheter surface, particularly when hydrated.

EXAMPLE 2

A different aqueous coating solution was prepared from:

100 ml. of an aqueous emulsion containing 33 percent by weight of an aliphatic poly(urethane) structural plastic, the emulsion also containing 17.6 percent by weight of N-methyl pyrrolidone as a cosolvent, plus 1.7 weight percent of triethylamine, the balance being water (Neo Rez R962 ICI Resins).

100 ml. of the 1 percent poly(ethylene oxide)water mixture described in Example 1.

This mixture thus contained 17.5 percent of the aliphatic polyurethane, 0.5 percent of poly(ethylene oxide), 8.8 percent of N-methyl pyrrolidone, and 0.85 percent of triethylamine, all percentages being by weight.

Polyurethane cardiovascular diagnostic catheters of the type sold by the Cordis Corporation were cleaned with a Freon brand solvent, dried, and the mixed aqueous coating formulation applied by dipping or spraying. The catheters were dried at 60 degrees C. to provide an outer, friction-reducing coating 14 having a thickness of about 0.0007 inch. This coating also provided to the catheter a great reduction in its coefficient of friction upon hydration.

EXAMPLE 3

A dispersion of the following materials was made:

18.8 grams of any epoxy ester structural polymer (Epotuf 92-737, sold by Reichhold Chemicals);

Six hundred microliters of triethylamine and six hundred microliters of 2-dimethyl-amino ethanol, stirred together with the epoxy resin to mix them;

40 ml. of water, with sufficient stirring to achieve a homogenous dispersion of the ingredients.

Twenty-five ml. of the above-prepared dispersion was then mixed with 25 ml. of the one percent aqueous poly(ethylene oxide) dispersion used in Example 1. Such a mixture is then applied to a base material as a coating, the base material being made of a poly(esterurethane) compound DUCOR, which is a proprietary material of the Cordis Corporation. Good adhesion as well as good friction reduction was achieved, due to the presence of the poly(ethylene oxide).

EXAMPLE 4

A dispersion was prepared of 25 ml. of the aliphatic polyurethane aqueous dispersion used in Example 2 (Neo Rez R962);

25 ml. of the one percent poly(ethylene oxide)-water mixture described in Example 1, and;

900 microliters of an aqueous mixture of 5 volume percent of poly(ethylene imine) plus 20 weight percent of heparin. The heparin complexes with the poly(ethylene imine) apparently through ionic interaction.

When such a coating is placed on a polyurethane catheter in accordance with Examples 1 or 2 to form a thin coating over the outer surface of the catheter, such catheter exhibits greatly reduced coefficient of friction upon hydration, and also provides the gradual release of heparin to the localized tissues surrounding such a catheter in the human body. For example, such a catheter may be used for a well-known PTCA process or other procedure involving the coronary arteries, while the heparin released from the catheter coating may serve to suppress acute thrombosis, stenosis, or late restenosis after treatment.

The heparin-poly(ethylene imine) complex in the above formulation may be replaced with a heparin-benzalkonium chloride complex, dispersed in isopropyl alcohol, as an alternate technique for providing to a catheter or other device a lubricating, heparin-releasing coating. As a further alternative, such a catheter coating may contain a complex of heparin with tridodecylmethylammonium chloride as a substitute for the heparin complex described above. Other heparin complexes for use herein may be derived from: methacrylamidopropyltrimethylammonium chloride; trimethylammonium methylmethacrylate chloride; and 1-vinyl pyrrolidone (2-dimethylaminoethyl methacrylate) copolymer.

EXAMPLE 5

An aqueous dispersion of the following formula was prepared by mixing:

25 ml. of an aqueous emulsion of polyurethane in 32 weight percent concentration with with 2-3 weight percent triethylamine and 3-4 weight percent methylethylketone (Andur WB-50 of Anderson Development Corp.); this polyurethane has some aryl groups;

75 ml. of water; and 100 ml. of the poly(ethylene oxide) aqueous dispersion of Example 1.

The resulting coating solution may be applied to a polyurethane catheter as described in Example 1 to provide an extremely uniform lubricating coating.

Primers may be used as desired to increase adhesion of the friction-reducing coatings of this application to the base material, such as a catheter.

That which is claimed is:

1. A plastic catheter formed of a base material having a friction-reducing coating carried on the outer surface of said base material, said friction-reducing coating being of the type that provides friction-reduction on hydration thereof, said coating comprising an intimate physical mixture of 50 to 98 weight percent of a structural plastic material and 2 to 50 weight percent of poly(ethylene oxide), said base material consisting essentially of a plastic essentially free of said poly(ethylene oxide).

2. The catheter and base material of claim 1 in which said structural plastic material is polyurethane.

3. The catheter and base material of claim 2 in which said base material is polyurethane.

4. The catheter and base material of claim 2 in which said polyurethane is aliphatic.

5. The catheter of claim 1 claim 1 in which the coating is carried on the outer surface of a plastic catheter, said coating having a thickness of about 0.0001 to 0.05 inch.

6. The catheter and base material of claim 1 in which the molecular weight of said poly(ethylene oxide) is at least about one million.

7. The catheter and base material of claim 1 which the coating also contains an effective amount of a therapeutic agent.

8. The catheter of claim 7 in which said structural plastic material is polyamide.

9. In a plastic catheter having a friction-reducing coating carried on the outer surface of said catheter, said friction-reducing coating being of the type that provides its maximum friction reduction on hydration thereof, the improvement comprising, in combination:

said coating comprising an intimate physical mixture of 50 to 98 weight percent of a plastic material having hydrophobic characteristics, and 2 to 50 weight percent of poly(ethylene oxide) having a molecular weight of at least about one million.

10. The catheter of claim 9 in which the thickness of said coating is about 0.0001 to 0.05 inch.

11. The catheter of claim 9 in which the plastic material is polyurethane.

12. The catheter of claim 11 in which the catheter itself which carries said coating is also made of polyurethane.

13. The catheter of claim 9 in which said coating also contains an effective amount of a therapeutic agent.

14. In a plastic catheter having a friction-reducing coating carried on the outer surface of said catheter, said friction-reducing coating being of the type that provides friction reduction on hydration thereof, the improvement comprising, in combination: said coating comprising an intimate physical mixture of 50 to 98 weight percent of a plastic material having hydrophobic characteristics, and 2 to 50 weight percent of poly(ethylene exide) having a molecular weight of at least 10,000, the thickness of said coating being about 0.0001 to 0.05 inch.

15. The catheter of claim 14 in which the molecular weight of said poly(ethylene oxide) is at least one million.

16. The catheter of claim 14 in which said coating also contains an effective amount of a therapeutic agent.

17. The catheter of claim 14 in which said plastic material is polyamide.

18. The plastic catheter of claim 14 in which the plastic material is polyurethane.

* * * * *